United States Patent [19]

Wagner

[11] 4,278,888
[45] Jul. 14, 1981

[54] APPARATUS FOR DETERMINING THE SPATIAL DISTRIBUTION OF THE ABSORPTION OF RADIATION IN A BODY

[75] Inventor: Wolfgang Wagner, Hamburg, Fed. Rep. of Germany

[73] Assignee: U.S. Philips Corporation, New York, N.Y.

[21] Appl. No.: 5,734

[22] Filed: Jan. 23, 1979

[30] Foreign Application Priority Data

Jan. 21, 1978 [DE] Fed. Rep. of Germany ....... 2802593

[51] Int. Cl.³ .......................................... G03B 41/16
[52] U.S. Cl. ................................. 250/445 T; 250/491
[58] Field of Search ........................... 250/445 T, 491

[56] References Cited

U.S. PATENT DOCUMENTS

| 4,075,489 | 2/1978 | Neal | 250/445 T |
| 4,117,337 | 9/1978 | Staats | 250/445 T |
| 4,158,776 | 6/1979 | Barrett | 250/445 T |

Primary Examiner—Craig E. Church
Attorney, Agent, or Firm—Thomas A. Briody; Robert T. Mayer; Jack E. Haken

[57] ABSTRACT

A computed tomography device wherein a body contour outside an examination area is determined by measurements made with the aid of an auxiliary radiation source (for example light or ultrasound).

9 Claims, 7 Drawing Figures

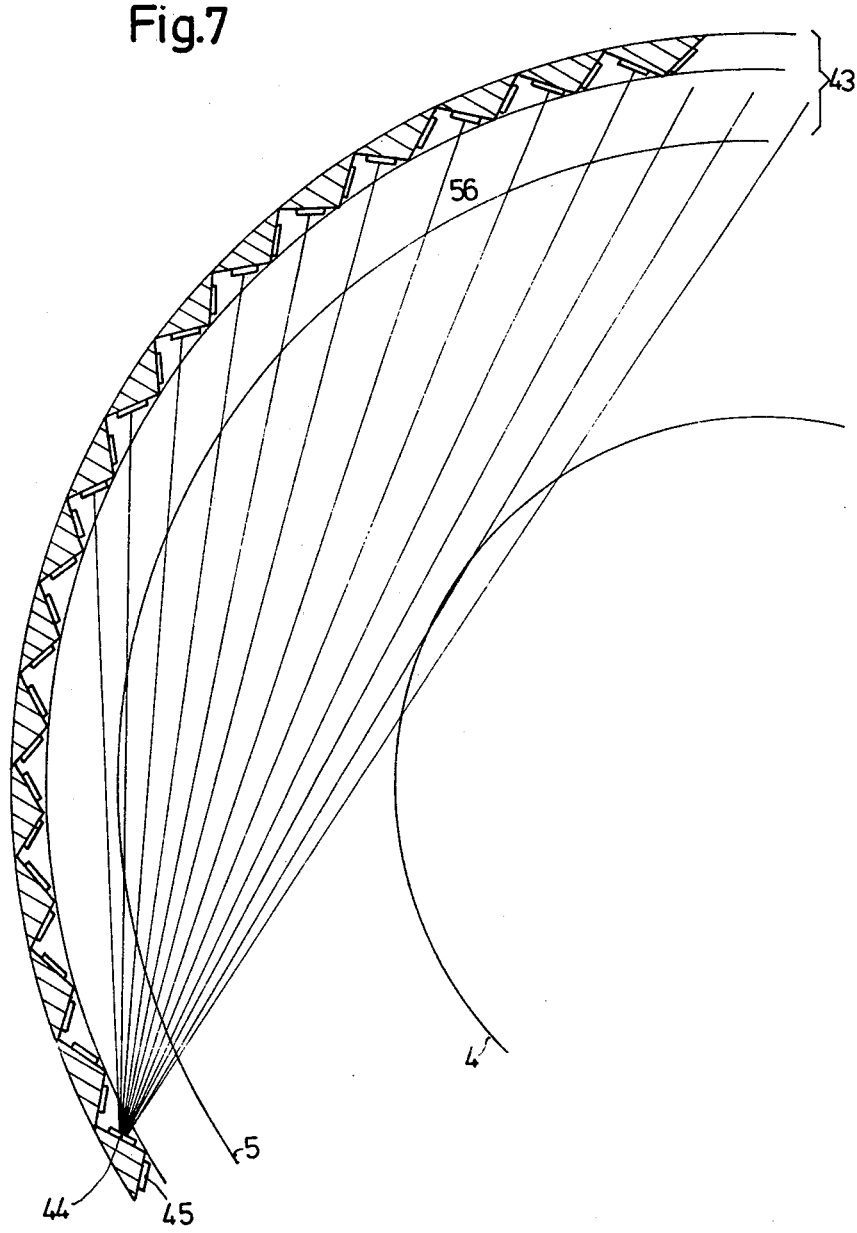

APPARATUS FOR DETERMINING THE SPATIAL DISTRIBUTION OF THE ABSORPTION OF RADIATION IN A BODY The invention relates to an apparatus for determining the spatial distribution of the absorption of radiation in a body from a plurality of measuring series where each series represents a sequence of measuring values of the integral of the absorption of the body along one of a multitude of measuring beam paths. The apparatus comprises at least one radiation source, which irradiates an area being examined, and a detector array, which detects the intensity of the radiation on the other side of the body and which supplies the measuring values. A positioning area body, which is larger than and surrounds the area being examined is provided.

Such an apparatus is known from German Offenlegungsschrift No. 24 39 847. In that apparatus a principal radiator and detector array is rotated about an axis which is perpendicular to an examination plane during a measurement. The area is examined being a circular area which is concentric with the axis, and is irradiated by the radiation beam emitted by the radiation source in all positions of the radiator and detector array system. A disadvantage of such an arrangement is that the body slice should be situated completely within the area being examined. Thus, there should be no part of the body slice from which measuring values cannot be obtained in any measuring direction, otherwise serious errors will occur during subsequent reconstruction of the absorption distribution in the area being examined i.e. in the area which is scanned by measuring beams in every direction. In the case of the known equipment the area being examined should therefore be large enough that bodies having particularly great cross-sectional areas may be positioned completely within the area.

Generally only a limited image area is of interest for diagnosis, for example of an organ inside the human body. Therefore, it is desirable to restrict the derivation of measuring values to said location, while avoiding the said reconstruction errors, so that the radiation dose administered to the patient is reduced and a complete measurement is possible with a smaller number of measuring cycles. For equipment in which the radiator/detector system is laterally shifted during the measurement this means that the required measuring time and thus the image errors caused by patient movements are reduced; in third generation X-ray scanners in which the radiator/detector system is only rotated about an axis which is perpendicular to the area being examined, this means that the number of detectors, and thus the system costs can be reduced.

German Application No. P 27 53 260 describes a method for determining the spatial distribution of the radiation absorption, which enables the absorption distribution in the area being examined to be reconstructed, even if the body is not completely covered by the radiation from the radiation source in specific directions (i.e. when the body is situated partly outside the area being examined). However, the method described therein fails if the body to be examined is not completely covered by the radiation in at least one direction. This method is based on a calculation of the body contour. However, outside the area being examined this is only possible by interpolation of the body contour which is situated within the area which can be determined by measurement. This gives rise to errors which increase that part with the fraction of the body contour which is located outside the area and which can only be determined by interpolation.

It is the object of the present invention to provide an apparatus which allows a smaller area to be examined and, in spite of this, enables the absorption in the area being examined to be determined, even if part or all of the body contour is situated outside the area being examined.

According to the invention this object is achieved by providing at least one auxiliary radiation source which emits auxiliary radiation which is strongly absorbed by the body (at least in an area which directly adjoins the area being examined) and which is tangent to the positioning area, and auxiliary detectors are also provided which respond to the auxiliary radiation falling outside the area being examined and which supply signals which are dependent on the distance of the rays which are tangent to the body from the area being examined.

The auxiliary radiation may be less harmful to the patients than the X-ray or gamma radiation which is used for the examination.

The invention is based on the recognition that the contour of a body—at least outside the area being examined—can be determined if the position of rays which are emitted by the auxiliary radiation source or sources and which are tangent to the body outside the area being examined is known and that the absorption distribution within the area being examined can be reconstructed if the shape of the body contour is known and measuring values corresponding to the area being examined have been determined.

If a body is only partly covered by the measuring rays which extend parallel to each other in a specific direction and which completely pass through the area being examined, but the body is completely covered in another direction, the absorption distribution may be determined approximately as follows. (It is assumed here that the body contour is situated entirely outside the area being examined and the body contour is for example determined as follows).

For any position of the radiator/detector system there are two rays from the auxiliary radiation sources which are exactly tangent to the two outer edges of the body. These tangent rays are determined in all positions of the radiator/detector array system.

For a radial ray which intersects the center of the examination area at (an angle $\phi$ to the x-axis,) the intersections with all tangent rays are computed. The radial ray has an intersection with all tangents, which are not exactly parallel.

The intersection having the smallest distance to the center of rotation is determined. The X, Y coordinates of the intersection are subsequently used as body contour coordinates.

A set of measuring values which represents the absorption of the body along parallel radiation paths, is only representative of the absorption of the body in a limited inner area (in the area being examined (p) or in the region of interest (r), $p > |r|$). The further data are obtained as follows on basis of the body contour thus determined:

First a p-value greater than r is generated for each scanning angle. This p-value defines a ray which extends through the body at an angle over a distance p. Now those points x, y of the previously calculated body contour which are situated on this ray are determined. In this way two points with the coordinates, $x_1$, $y_1$ and $x_2$, $y_2$ are obtained. The distance between these two points, that is the length of the ray, is then calculated.

For all values of p outside the area being examined this computation is repeated. The interval between the p-values then corresponds to the distance of two adjacent radiation paths, along which the absorption has been determined by measuring the X-radiation.

Each of the rays thus determined, whose length differs from 0, corresponds to an absorption value which follows from the product of this length and the absorption coefficient of water. These computations are repeated for all scanning directions.

The values thus determined are processed as though they have been obtained by measuring the absorption, and together with the actual measuring values they are processed in known manner to obtain the reconstruction. This gives rise to errors because it is assumed that the absorption in the tissue outside the area being examined is equal to that of water, but these errors are comparatively small, because the human body for the greater part consists of water and the approximation of the absorption values outside the area being examined only influences the accuracy of the absorption values inside the area being examined to a comparatively small extent.

The invention will now be described in more detail with reference to the drawings.

FIG. 7 shows an arrangement of auxilary radiation sources and auxilary detectors in the apparatus of FIG. 6.

Figure 1:
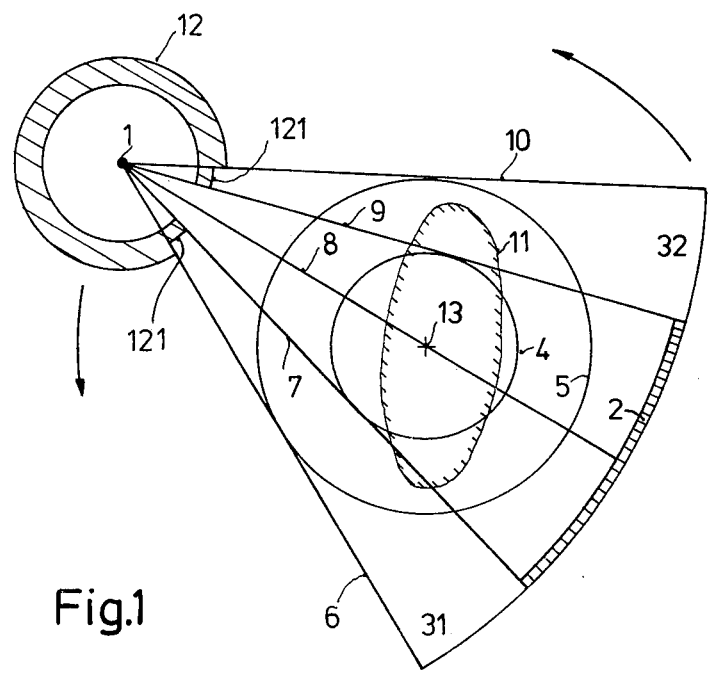
FIGS. 1 and 2 show first embodiments of the invention.

FIG. 1 represents a third generation scanner (i.e. a scanner in which a principal X-ray radiator 1 and a principal detector array 2, are rotated about an axis 13 which is perpendicular to a circular area being examined (hereinafter referred to as the examination area) 4. A collimator 12 is rigidly connected to the X-ray radiator 1. The collimator stops down a fan-shaped radiation beam with the marginal rays 7 and 9, which are exactly tangent to the examination area 4. The central ray, which extends through the axis of rotation 13, is designated 8. The detector array 2, which is arranged on the other side of the body 11 relative to the radiator, has such dimensions in the examination plane such that it can receive the entire radiation beam including the marginal rays 7 and 9. So far the apparatus is identical to the prior art.

The collimator has dividing portions 121 and 122 on both sides of the fan-shaped radiation beam which allow sufficient radiation to pass through, so that auxiliary detectors 31 and 32, which are arranged on an arc with the detector array 2, can just detect the presence of unattenuated radiation. The marginal rays in the auxiliary radiation beam are designated 6 and 10 and their angle of aperture is selected so that the entire circular positioning area 5 within which the body 11 can be positioned is covered by the auxiliary radiation and the direct radiation from the radiation source 1. The auxiliary detector 31 and 32 produce a signal which, (as will be explained with reference to FIGS. 2 and 3) is only dependent on the position of an auxiliary ray (not shown) which is tangent to the body 11, In the embodiment of FIG. 1 the auxiliary radiation is generated by the same radiation source as the radiation which passes through the examination area, i.e. the auxiliary radiation source and the actual radiation source are identical in this case. This is a disadvantage because on the one hand, the body outside the examination area is also exposed to X-rays—though attenuated and, on the other hand, the auxiliary radiation is not completely absorbed by the body 11, so that the signals supplied by the auxiliary detector arrays 31 and 32 will not only depend on the distance of the ray that is tangent to the body 11 to the axis of rotation 13, but also on the extent to which the auxiliary radiation is attenuated by the body 11.

Figure 2:
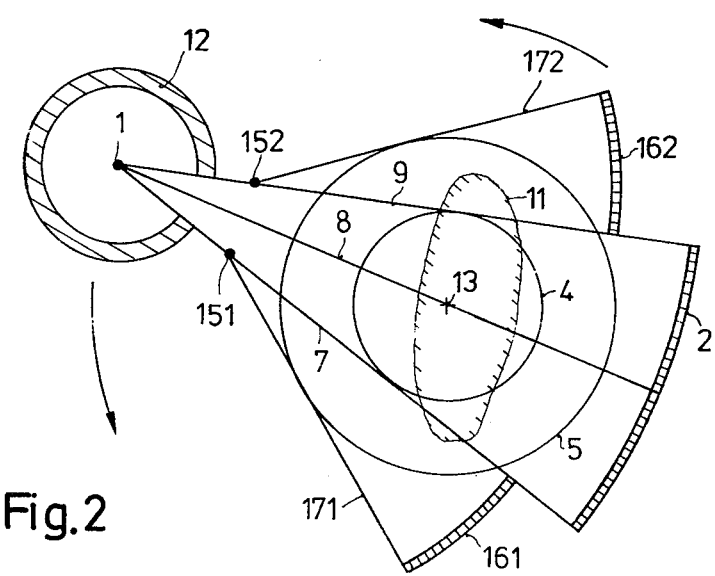

FIG. 2 shows an embodiment which does not have these drawbacks. (Corresponding parts again bear the same references as used in FIG. 1). In the apparatus of FIG. 2 the auxiliary radiation is produced by two auxiliary radiation sources 151 and 152 which emit optical radiation. The sources are arranged in the direct vicinity of the marginal rays 7 and 9 in such a way that the light emitted by them is tangent both to the examination area 4 and to the positioning area 5 (the rays which are tangent to the positioning area are designated 171 and 172). Two auxiliary detectors arrays 161 and 162, are provided for measuring the auxiliary radiation which comprise a plurality of separate detectors which respond to the emitted auxiliary radiation, and which are arranged around the auxiliary radiation sources 151 and 152 respectively on a circular arc.

The auxiliary detectors 161 and 162 may be arranged so that they are an extension of the detector array 2, but this is not absolutely necessary. It is, however, essential that the auxiliary radiation sources 151 and 152 and the auxiliary detector arrays 161 and 162 are arranged in the same plane as the radiation source 1 and the detector array 2, or in a plane which is parallel to the plane through which the radiation from the radiation source passes and which is disposed at a small distance from that plane. The radiation source and the auxiliary radiation source will then cover substantially the same cross-sectional area. The auxiliary radiation sources 151 and 152 may be light-emitting diodes which emit visible light or laser diodes which emit infrared light. It is even more advantageous to couple two optical fibre guides to a common light source. The ends of the fibers are disposed as closely as possible to the marginal rays 7 and 9 at the locations 151 and 152 in such a way that their light is directed towards the auxiliary detector arrays 161 and 162. The auxiliary radiation sources and the auxiliary detector arrays, together with the radiation source 1 and the detector array 2, are rotated about the axis 13, (i.e. they should be rigidly connected to the measuring arrangement comprising the radiation source 1 and the detector array 2) if the auxiliary radiation sources and the auxiliary detector arrays operate in an amplitude, frequency, or pulse-modulated mode, the measurement of the auxiliary radiation will be less sensitive to stray light and the effects of noise.

Figure 3:
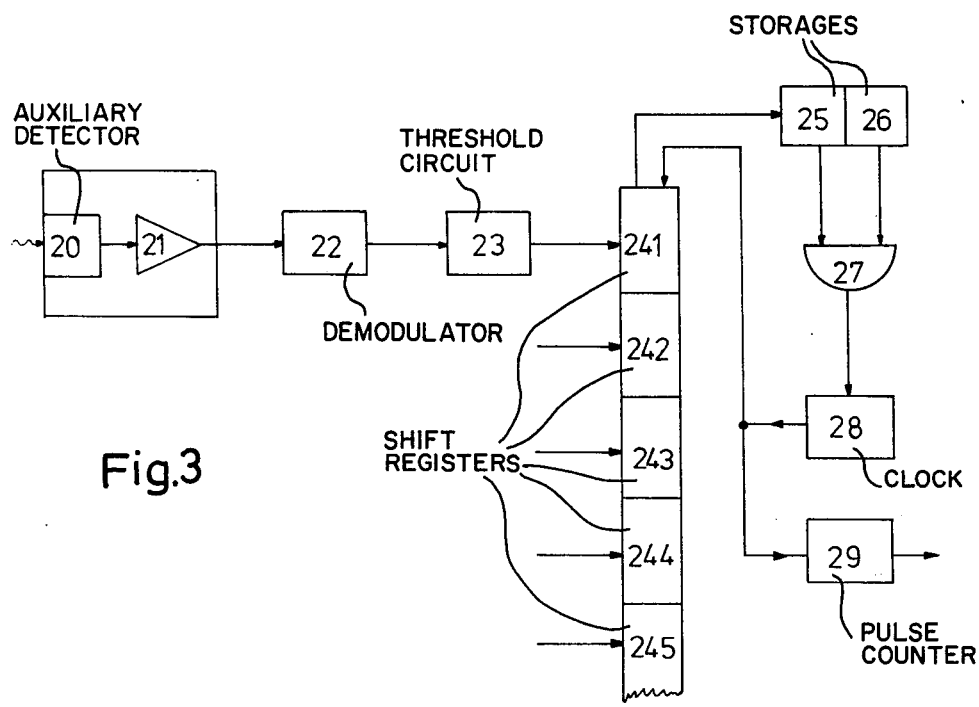
FIG. 3 shows a circuit for processing the signals supplied by apparatus in accordance with FIG. 1.

FIG. 3 shows a circuit which is suitable for processing the signals supplied by an auxiliary detector 20, which is integrated with a preamplifier 21. The output signal of the preamplifier is applied to a demodulator which, in the case that the auxiliary radiation is amplitude-modulated, may comprise a band-pass filter followed by an amplitude detector. The output signal is applied to a threshold circuit 23, which is designed so that its threshold value is greater than the noise amplitude produced by the preceding elements and is sufficiently low to detect the radiation which is produced by the auxiliary radiation sources and which is not attenuated by the body. Each auxiliary detector is provided with an identical chain of elements 21 to 23. The output values (logic 1 or 0) of all threshold amplifiers are simultaneously entered into the cells of a shift register. Once per measuring cycle, FIG. 3 shows only cells 241 to 245 of the shift together. Subsequently, a clock generator 28 becomes operative. Pulses from the clock generator cause the stored data to be consecutively entered into the storage elements 25 and 26. An exclusive OR-circuit 27 supplies a stop pulse to the clock generator 8 if the contents of the memories 25 and 26 are complementary (for example 0, 1 or 1, 0 respectively), which means that in one of the memories 25, 26 a signal is stored from an auxiliary detector which has just been exposed to auxiliary radiation, while the adjacent auxiliary detector is masked by the body 11. The pulse counter 29 records the number of clock pulses produced prior to the appearance of the stop pulse and transfers this number to a computing unit (not shown) for determining the body contour. The number of pulses characterizes the position of the auxiliary ray which is tangent to the body 11; from this data, from the angular position of the radiator/detector system, and the geometrical arrangement of the auxiliary radiation sources 151 and 152, the auxiliary detector arrays 161 and 162 the position of the ray which is tangent to the body can be determined. When the ray which is tangent to the body is also determined in the other positions of the radiator/detector system, the body contour is represented by the envelope of all rays which are tangent to the body. The data lines from a computer necessary for controlling and driving the circuit of FIG. 3 are not shown. For this circuit it is essential that for each measurement, i.e. per angular position of the radiator/detector only two data words are generated (one for each auxiliary detector array 161 and 162) which characterize the positions of the auxiliary rays which are tangent to the body, so that the data flow and thus the requirements imposed on the data lines and the following computing units are not stringent. Moreover, the measurements of the auxiliary detector array and the operation of the circuit shown in FIG. 3 need not be synchronized with the measurements and computations for determining the absorption profile.

Figure 4:
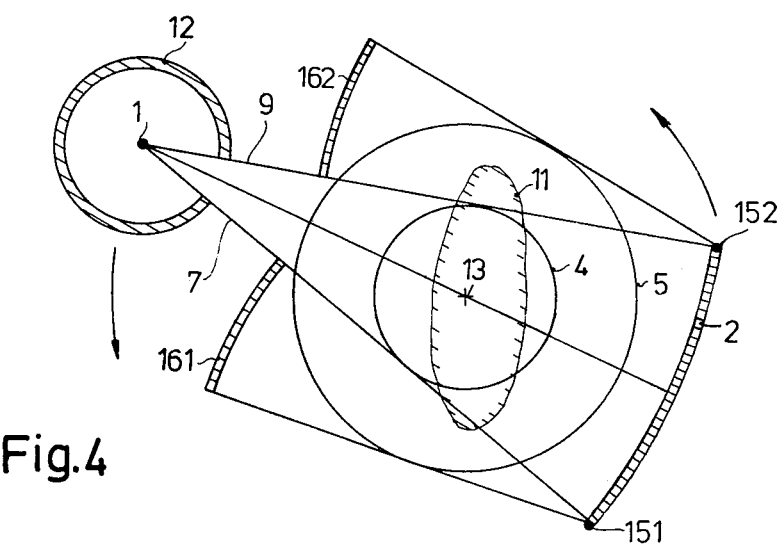
FIGS. 4–6 show further embodiments of the invention.

FIG. 4 shows an apparatus in which the positions of the auxiliary radiation sources 151 and 152 and the auxiliary detector arrays 161 and 162 have been interchanged. The auxiliary radiation sources are arranged at the detector array end of the arc while the auxiliary detector arrays 161 and 162 are arranged near the radiation source 1 so that they adjoin the marginal rays 7 and 9 and the auxiliary rays which are tangent to the positioning area 5. This results in a more compact construction.

Figure 5:
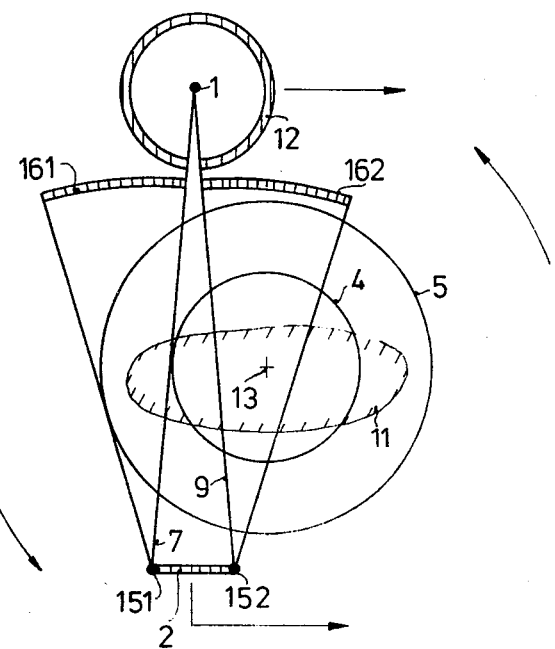

FIG. 5 shows a second generation embodiment with an X-ray scanner. The radiation beam 7, 9 from the radiation source 1 is bounded by the radiation source 12 so that in any position of the radiator/detector for obtaining all the measuring values within the scanning area only a part of the examination area is covered. The radiator/detector in such scanners is first translated in the latteal direction, and is subsequently rotated through a small angle followed by another lateral movement. In the position shown in FIG. 5 the auxiliary radiation emitted by an auxiliary radiation source 152 which is arranged at one end of the detector array 2, is completely absorbed by the body 11, while the auxiliary radiation from the auxiliary radiation source 151 which is disposed at the other end of the detector array is only partly absorbed by the body 11 thus, by means of the auxiliary detector array 161 the position of the left-hand tangent ray can be determined. Upon each further movement to the right, the position of the left-hand tangent ray changes. After several lateral movements the radiation emitted by the auxiliary radiation source 152 past the body 11 reaches the auxiliary detector array 162, so that the position of the tangent rays on the right-hand side of the scanning area 4 is determined.

It has been assumed that the auxiliary detector arrays comprise separate series-connected auxiliary detector elements. However, it is alternatively possible to employ an auxiliary detector array which comprises only one single elongate auxiliary detector. This auxiliary detector supplies a signal whose amplitude or integral value exactly corresponds to the irradiated portion of the total area of the auxiliary detector; the position of the ray which is tangent to the body can be derived therefrom. It is alternatively possible to use a light source, which emits a very narrow beam, which is deflected over the associated auxiliary detector array by means of a rotating deflection mirror ($151_a$, $152_a$ in FIG. 2).

It is also possible to use ultrasound as the auxiliary radiation. A plurality of ultrasound transmitters may be provided in accordance with the principle of the so-called phased arrays. They are actuated simultaneously at the same frequency but with different phase; the phase or phase differences between the individual transmitters being changed continuously by suitable delay circuits. Thus, the direction of the sound wave is constantly changed so that it is deflected along the surface of the associated receiver on the other side of the examination area.

Figure 6:
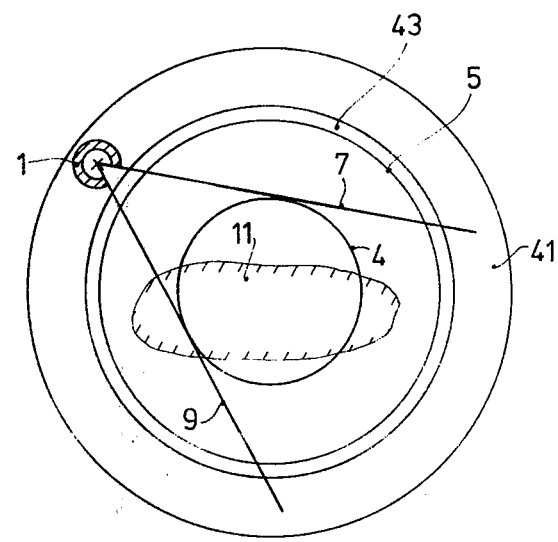

FIG. 6 shows an apparatus which, for each angular direction of a measuring profile, comprises an X-radiation source (for the sake of convenience the drawing shows only one X-radiation source 1); the sources (not shown) are arranged opposite the detector arrays, in a circular orbit around the body 41. The effective angular range of a single X-radiation source is thus limited to 30° to 40° so that only a comparatively small area 4 can be covered by the measuring beams from all radiation sources. In such an apparatus all radiation sources are switched on simultaneously or briefly after each other, so that a very short measuring time is obtained. This enables the absorption distribution of moving objects, for example a heart, to be determined.

A stationary (non-moving) arrangement of auxiliary radiation sources and auxiliary detectors is provided at the location 43 for determining the contour of the body which is partly situated outside the examination area.

FIG. 7 shows a detail of FIG. 6. The inner side of the orbit 43 is sawtooth. An auxiliary radiation source 44, preferably an infra-red light emitting diode, and an auxiliary detector 45, preferably a photo diode which is sensitive to infra-red radiation with an integrated photo amplifier is mounted on each sawtooth. The slope of the two sawtooth surfaces is such that the surface carrying the auxiliary source 44 is perpendicular to an auxiliary ray 56 which extends midway between the scanning area 4 and the positioning area 5. The area, which surrounds the body in annular form, is small, for example 1 cm, and is disposed above or underneath the plane in which the absorption of the X-rays by the body is determined, in order to ensure that the radiation path of the individual X-radiators is not disturbed. In this respect it is assumed that the contour of a body in such an adjoining plane deviates only slightly from the contour to be determined. A sufficient number of sawteeth which are uniformly divided over the circumference of the zone 43 are provided, preferably 200. The auxiliary radiation is measured so that, under control of a switching device (not shown) the auxiliary radiation sources 44 are switched on consecutively in their natural sequence and each time the signals from the auxiliary detectors situated in the range of the emitted auxiliary rays are determined by a circuit arrangement which is similar to the arrangement in FIG. 3. The shape of the sawtooth is selected so in relation to the radii of the examination area 4, the positioning area 5 and the area 43 so that the auxiliary rays which are just tangent to the examination area or the positioning area are not totally reflected by the auxiliary detectors and so that adjacent sawteeth do not mask each other.

The invention in the embodiments described may also be used in radionuclide scanners.

What is claimed is:

1. In apparatus for determining the spatial distribution of the absorption of radiation in a body of the type which includes principal radiation source means which radiate an examination area with penetrating radiation and principal detector means disposed opposite the principal source means, which detect the intensity of radiation from the principal source means which passes through the body, and which further defines a positioning area for placement of the body, which area is larger than and surrounds the examination area, the improvement comprising:

auxiliary radiation source means which emit auxiliary radiation into an area which includes an outer boundary of the examination area and which is tangent to an outer boundary of the positioning area, the auxiliary radiation being strongly absorbed by the body, and a auxiliary detector means which respond at least to auxiliary radiation falling outside the examination area and which supply signals which are a measure of the distance between auxiliary radiation rays which are tangent to the body and the boundary of the examination area.

2. The improvement of clam 1 wherein: the principal detector means comprise a detector array which rotates around the body in coupled relationship with the source means, the auxiliary radiation source means comprise two auxiliary radiation sources each of which irradiates an area which directly adjoins the examination area, and wherein the auxiliary detector means comprise two auxiliary detector arrays which are disposed adjacent the radiation beam produced by the principal radiation source means and which rotate with the detector array.

3. The improvement of claim 2 wherein the auxiliary radiation sources are disposed adjacent the principal radiation source means and the auxiliary detector arrays are disposed adjacent the detector array.

4. The improvement of claim 2 wherein the auxiliary detector arrays are arranged adjacent the principal radiation source means and the auxiliary radiation sources are disposed adjacent the detector array.

5. The improvement of claim 1 wherein the examination area is planar, the principal radiation source means comprise a plurality of stationary radiators and the principal detector means comprise a plurality of stationary detector arrays, the radiators and arrays being disposed in a first annular zone which surrounds the examination area, the auxiliary radiators and auxiliary detectors being disposed at uniformly spaced intervals in a second annular zone in a plane which is spaced from the plane of the examination area.

6. The improvement of claim 5 wherein the second annular zone includes a plurality of sawtooth protruberances having peaks pointing toward the center of the first annular zone, an auxiliary radiator being disposed on a first side of each protruberance and an auxiliary detector being disposed on a second side of each protruberance.

7. The improvement of any of claims 1 through 4 wherein the auxiliary detector means comprise an elongate auxiliary detector which functions to determine the location of a ray tangent to the body by producing a signal whose amplitude corresponds to that fraction of the elongate detector which is exposed to auxiliary radiation.

8. The improvement of any of claims 1 through 4 wherein the auxiliary detector means comprise a plurality of adjacent auxiliary detectors and further comprising comparator means which function to compare signals supplied by each pair of adjacent auxiliary detectors and which produce a signal if one of the pair receives auxiliary radiation which has been attenuated by the body and the other of the pair receives radiation which has not been attenuated by the body.

9. The improvement of claim 7 wherein the auxiliary radiation source means comprise means for deflecting rays of auxiliary radiation.

* * * * *

UNITED STATES PATENT AND TRADEMARK OFFICE
CERTIFICATE OF CORRECTION

PATENT NO. : 4,278,888
DATED : July 14, 1981
INVENTOR(S) : Wolfgang Wagner

It is certified that error appears in the above-identified patent and that said Letters Patent is hereby corrected as shown below:

Column 7, line 41, claim 1, delete "a"
Column 7, line 48, claim 2, "clam" should be --claim--
Claim 6 should read as follows:

-- 6. The improvement of claim 15 wherein the second annular zone includes a mounting structure having a plurality of sawtooth peaks directed toward the center of the first annular zone, an auxiliary radiator being disposed on a first side of each peak and an auxiliary detector being disposed on a second side of each peak. --.

Signed and Sealed this

Eighth Day of February 1983

[SEAL]

Attest:

GERALD J. MOSSINGHOFF

Attesting Officer   Commissioner of Patents and Trademarks